United States Patent [19]

Silber

[11] Patent Number: 5,498,252
[45] Date of Patent: Mar. 12, 1996

[54] TOXICITY RESISTANT, SELF-FITTING AND ADJUSTABLE, SELF-CLOSING TAMPON STRUCTURE

[76] Inventor: Arthur L. Silber, 543 Dobbins Dr., San Gabriel, Calif. 91775

[21] Appl. No.: 363,920

[22] Filed: Dec. 27, 1994

Related U.S. Application Data

[63] Continuation-in-part of Ser. No. 228,503, Apr. 15, 1994, Pat. No. 5,476,455, which is a continuation-in-part of Ser. No. 2,642, Jan. 11, 1993, Pat. No. 5,342,331.

[51] Int. Cl.$^6$ .............................. A61F 13/24; A61F 13/34
[52] U.S. Cl. ........................................... 604/330; 604/904
[58] Field of Search .................................. 604/330, 354, 604/14, 904, 55

[56] References Cited

U.S. PATENT DOCUMENTS

| | | |
|---|---|---|
| 2,355,628 | 8/1944 | Calhoun . |
| 2,386,590 | 10/1945 | Calhoun . |
| 2,613,670 | 10/1952 | Sokolik .................... 604/330 X |
| 3,404,682 | 10/1968 | Waldron . |
| 3,491,758 | 1/1970 | Mullan . |
| 3,595,236 | 7/1971 | Corrigan et al. . |
| 3,626,942 | 12/1971 | Waldron . |
| 3,683,915 | 8/1972 | Voss . |
| 3,706,311 | 12/1972 | Kokx et al. . |
| 3,712,305 | 1/1973 | Wennerblom et al. . |
| 4,232,673 | 11/1980 | Bucalo . |
| 4,286,594 | 9/1981 | Cunningham . |
| 4,351,339 | 9/1982 | Sneider .................... 604/904 X |
| 4,486,191 | 12/1984 | Jacob .................... 604/330 |
| 4,857,044 | 8/1989 | Lennon . |
| 5,342,331 | 8/1994 | Silber et al. . |

FOREIGN PATENT DOCUMENTS

| | | |
|---|---|---|
| 1123155 | 5/1982 | Canada . |
| 2725003 | 12/1977 | Germany .................... 604/904 |
| 753294 | 7/1956 | United Kingdom . |

Primary Examiner—David H. Willse
Attorney, Agent, or Firm—William W. Haefliger

[57] ABSTRACT

A menstrual, flow-controlling tampon comprising a generally upright insertion tube having upper and lower ends; flow-receiving structure positioned within the tube to be bodily displaced and expelled from the upper end of the tube; the flow-receiving structure having a deployable portion configured to distend from a downward collapsed position to an upwardly deployed condition, to extend into engagement with vaginal walls associated with the cervix, and accommodation to length of vaginal barrel, following its being expelled from the tube; and removal structure associated with the receiving structure to effect withdrawal thereof away from the cervix, whereby upper extent of the deployable portion of the flow-receiving structure gathers to retain flow in the flow-receiving structure during withdrawal.

24 Claims, 5 Drawing Sheets

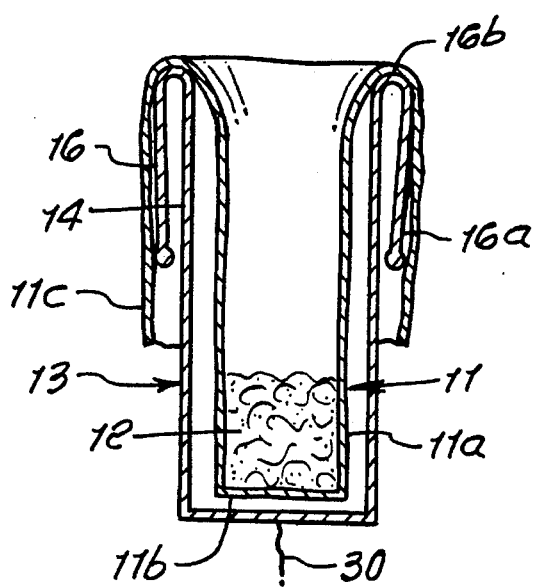
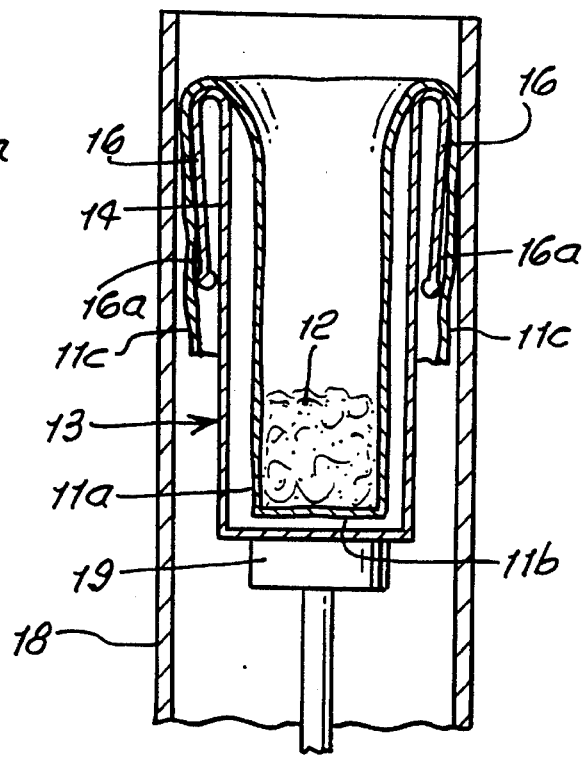
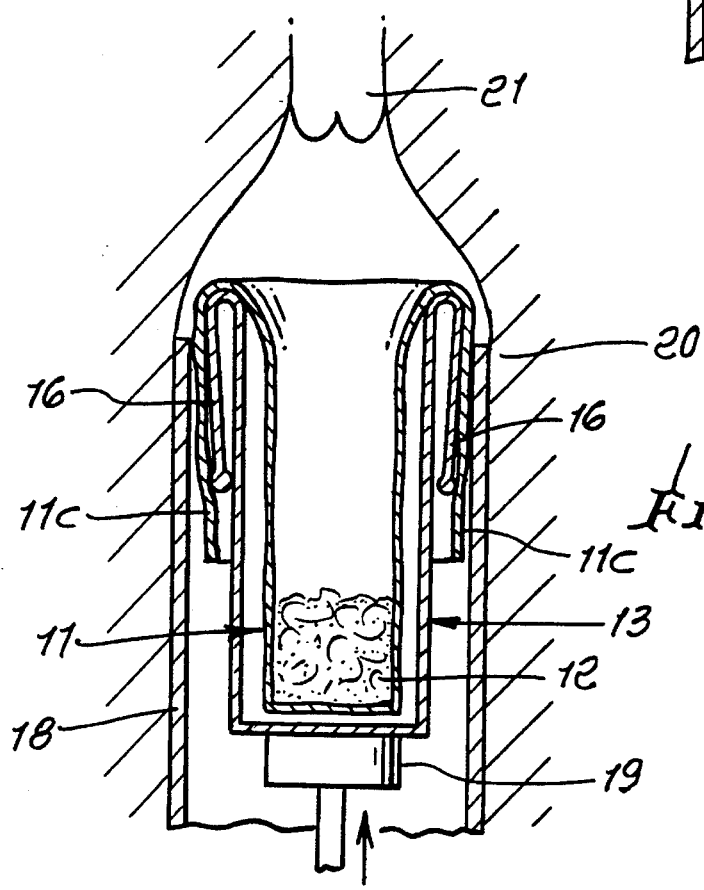

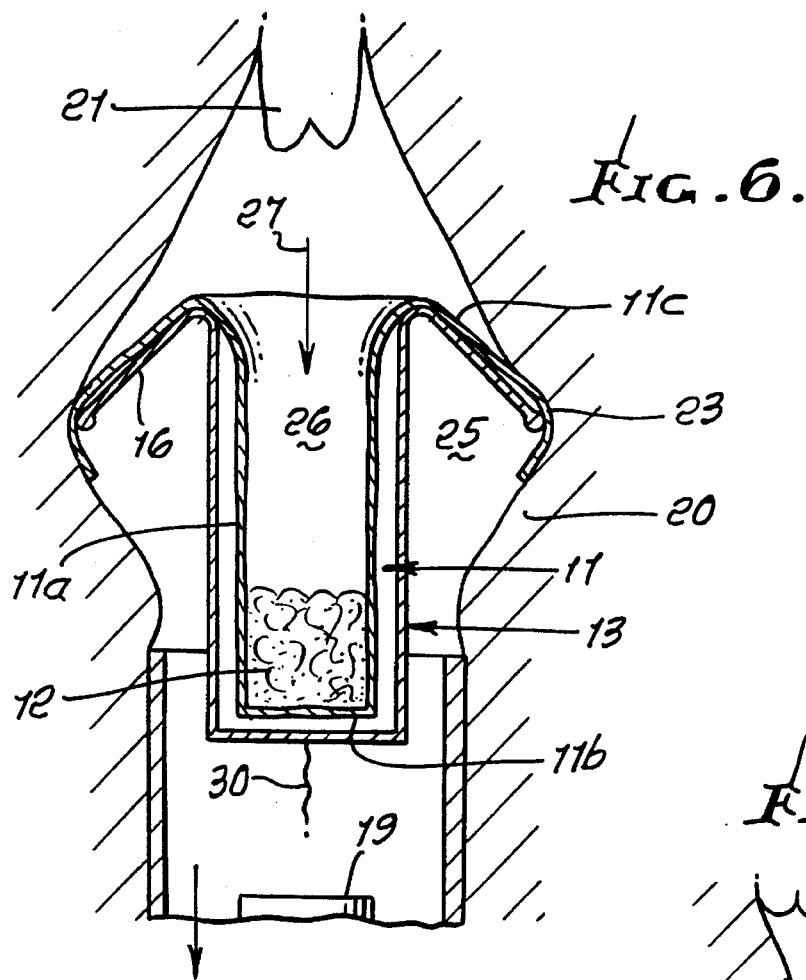
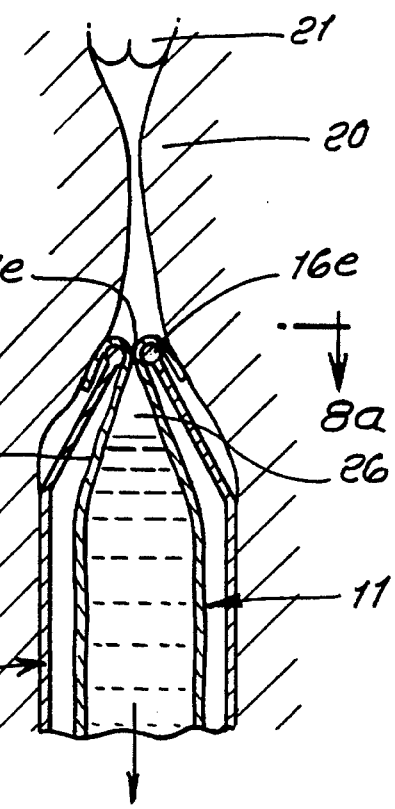
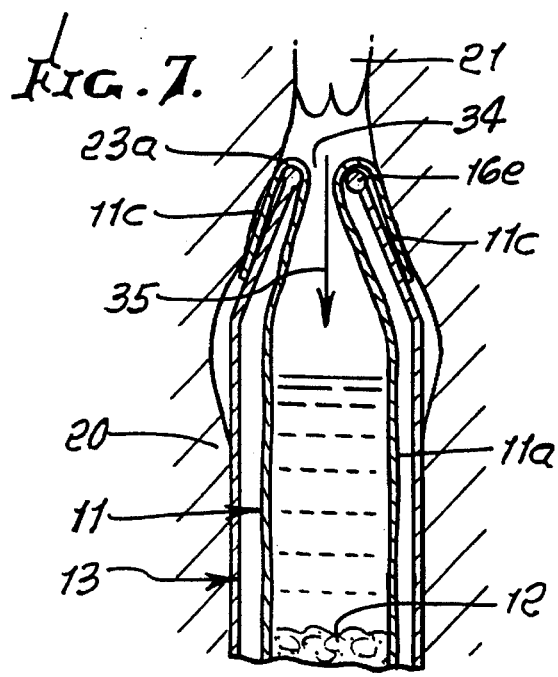

5,498,252

TOXICITY RESISTANT, SELF-FITTING AND ADJUSTABLE, SELF-CLOSING TAMPON STRUCTURE

This application is a continuation-in-part of Ser. No. 08/228,503 filed Apr. 15, 1994, now U.S. Pat. No. 5,476,455, which is a continuation-in-part of Ser. No. 08/002,642 filed Jan. 11, 1993, now U.S. Pat. No. 5,342,331, issued Aug. 30, 1994.

BACKGROUND OF THE INVENTION

This invention relates generally to flow-controlling tampons, and more specifically, to an improved tampon which controls and collects menstrual flow in such manner as to prevent toxic reaction.

In the past, flow-collection tampons were found to be objectionable, due to toxic reaction, as at tissue surfaces contacted by the collecting flow over periods of time. Also, prior tampons were found objectionable, due to flow leakage and contact with the user's hands, as during tampon removal.

There is need for improved tampon apparatus overcoming the above problems and difficulties, as well as providing additional and improved structural and functional features, as well as enhanced or better results, including protection and comfort in use.

SUMMARY OF THE INVENTION

It is a major object to provide improved tampon apparatus which meets the above needs.

Basically, the flow-controlling tampon of the present invention comprises:

a) a generally upright insertion tube having upper and lower ends, b) flow-receiving means positioned within the tube to be bodily displaced and expelled from the upper end of the tube, c) the flow-receiving means having a deployable portion configured to distend from a downward collapsed position to an upwardly deployed condition, to extend into engagement with vaginal walls associated with the cervix, and accommodation to length of vaginal barrel, following its being expelled from the tube, d) and removal means associated with the receiving means to effect withdrawal thereof away from the cervix, whereby upper extent of the deployable portion of the flow-receiving means gathers to retain flow in the flow-receiving means during withdrawal.

As will be seen, the flow-receiving means typically comprises a flexible film receptacle opening upwardly toward the cervix and having a flexible wall defining the deployable portion. In one form of the invention, the flexible wall defines annular corrugations which are self-expansible, upwardly, in conjunction with the flexible wall being expelled from the tube.

It is another object of the invention to provide the deployable portion of the flow-receiving means with terminals which self-interengage when gathered to retain flow in the flow-receiving means during withdrawal.

A further object is to provide a flow-receiving means which includes a sleeve carrying the flow receptacle. The sleeve may incorporate structure which urges the flexible wall of the receptacle into deployed condition, after or as the sleeve and flexible wall emerge from the insertion tube. Such structure may include multiple memory arms self-deployable in bending mode from downwardly collapsed positions in which the flexible wall of the receptacle fits over the arms, to self-urged, progressively upwardly, deployed position, in which the flexible wall is urged adjacent vaginal walls.

Yet another object is to provide such structure, as for example memory arms, to have an upwardly, finally deployed position in which the flexible wall is gathered to isolate flow received in the flow-receiving, flexible, film receptacle during withdrawal. The arms are typically folded back downwardly alongside the sleeve in collapsed position; whereas, the arms project in cantilevered condition from and above the sleeve in the finally deployed position. Further, the arms typically have distal end portions that are self-urged toward one another in finally deployed position.

Further objects include the provision of elastomeric, flexible film, as for example latex, with terminals which self-interengage when gathered to retain flow in the flow-receiving means during withdrawal.

These and other objects and advantages of the invention, as well as the details of an illustrative embodiment, will be more fully understood from the following specification and drawings, in which:

DRAWING DESCRIPTION

FIG. 3 shows completion of down-turning of the device upper portion, whereby the lower receptacle portion is effectively re-entrant into the device upper portion;

FIG. 4 is like FIG. 3 but shows the re-entrant device installed in an insertion tube;

FIG. 5 is like FIG. 4 and shows the device inserted into the vagina;

FIG. 6 is like FIG. 5 but shows the device emergent from the downwardly removed insertion tube, with upper extent of the device deployed outwardly by sleeve arms to engage vaginal walls;

FIG. 7 is like FIG. 6 but shows the lower receptacle portion of the flow-receiving device displaced downwardly, and the upper extent of the device collapsing beneath the cervix;

FIG. 8 is a section taken on lines 8a—8a of FIG. 8;

DETAILED DESCRIPTION

Figure 1:
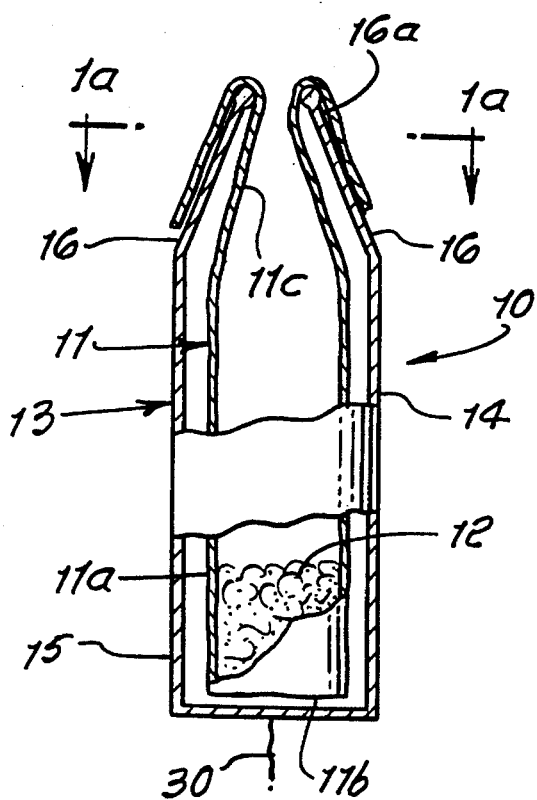
FIG. 1 is a vertical section showing an as molded condition of a flexible, generally tubular, flow-receiving means.

In FIG. 1, the flow receptor or receiving means 10 comprises an elastomeric film, such as latex, forming a flaccid, tubular body 11 having a receptacle-shaped lower portion, with a tubular wall 11a and bottom wall 11b. The upper walled extent 11c in as-molded condition, as shown, is to be closed together or gathered.

Figure 1A:
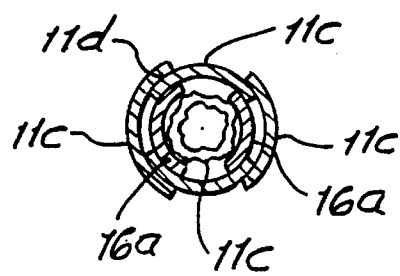
FIG. 1a is a section on lines 1a—1a of FIG. 1.

FIG. 1a shows upper extent 11c having overlapping leaves 11d. Flow-absorbing or wicking material 12 is introduced into the interior of the lower portion of the device, to receive menstrual flow. A semi-rigid, plastic or elastomer sleeve 13 has a tubular body with side wall 14 and lower wall 15 forming a receptacle. The sleeve has structure, such as cantilever arms 16, projecting upwardly, and tapering inwardly at 16a, in as-molded condition. The arms always seek that position, despite being bent downward, as in FIGS. 2–6. Sleeve 13 carries within it the flaccid film receptacle 11a and 11b elements.

Figure 2:
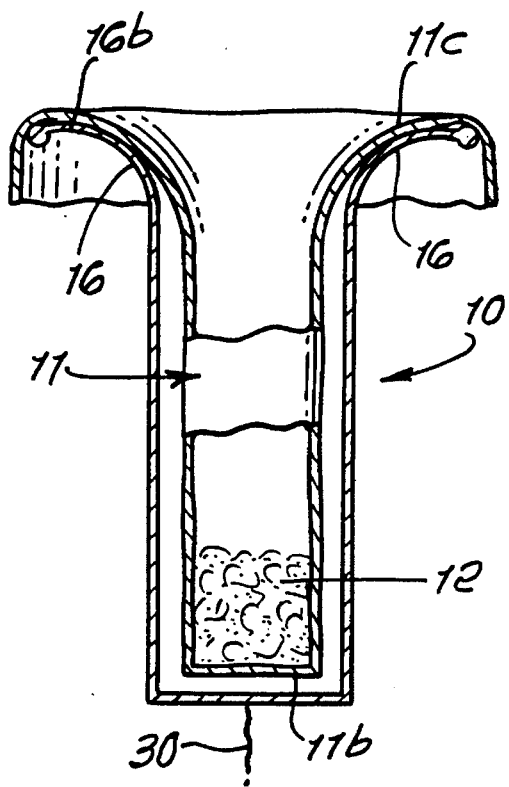
FIG. 2 is like FIG. 1 but shows upper extent of the device being turned back downwardly, annularly.

During assembly, the arms 16 are forcibly bent downwardly, as in FIGS. 2 and 3; and the flow-receiving film upper portion 11c is draped over the arm bends at 16b, to hang downwardly, as facilitated by their leaf structure seen in FIG. 1a. Such an assembly of 10 and 13 is assembled into the insertion tube 18, above a pusher 19, as in FIG. 4, that tube blocking radially outward movement of bent arms 16 seeking to restore to FIG. 1 position. Receptor portion 11d is thus re-entrant into 11c, which hangs as a skirt outside arms 16.

In use, the assembly of 10, 13 and 18 is inserted into the vagina, as indicated at 20 in FIG. 5, in alignment with the cervix 21. The pusher 19 is then manipulated to push the assembly of 10 and 13 relatively upwardly, and the tube 18 is withdrawn downwardly. As a result, the bent arms 16 are free to move radially outward, as they seek to restore to FIG. 1 position. The downwardly hanging upper extent 11c of the flow-receiving device 11 is thereby urged outwardly into sealing engagement with vaginal walls, as at loci 23 in FIG. 6, to stabilize the position of the assembly in the vaginal cavity 25, and sealing off the flow so that it enters the interior 26 of the receptor portion 11a via the cup-shaped upper extent 11c of the receptor. See arrows 27 in FIG. 6.

FIG. 7 shows the arms 16 substantially unbent and self-restored upwardly, as the assembly of 10 and is initially withdrawn downwardly, as by partially pulling on a string 210 attached to 10 and/or 13. The arms 16 deflect the upper film portion 11c of the flow-receiving means 11, as shown, maintaining it in sealing contact with vaginal walls, as at loci 23a, closer to the cervix. Flow continues to be received downwardly via the reduced entrance 34 to the receptacle 11c, and into the absorbent material seen at 12. See arrows 35.

Figure 8A:
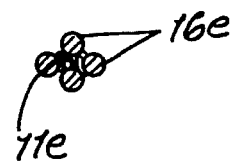
FIG. 8 shows the device being withdrawn from the vagina, the upper extent of the device self-collapsed to retain collected flow isolated in the device interior.

FIG. 8 shows the assembly 10 and 13 being withdrawn downwardly away from the cervix. This allows arms 16 to self-restore to FIG. 1 position, thereby acting to deflect the upper portion 11c of 11 into gathered and closed position, completely isolating the flow-receiving interior 26 of the receptacle Enlargements 16e molded integrally with the uppermost extents of the arms 16 press inwardly toward one another, closing the material of 11c together at 11e, as seen in FIG. 8a. Accordingly, the tampon or catamenial device may be manually retrieved with minimum finger exposure to menstrual flow, and no such exposure to flow collected in the device.

Referring to FIGS. 9–14, the modified device is similar to that of FIGS. 1–8; however, elements 10 and 13 of FIGS. 1–8 are integrated into one element, which has a self-closing upper position; i.e., need for a separate sleeve with biasing arms 16 is eliminated.

Figure 9:
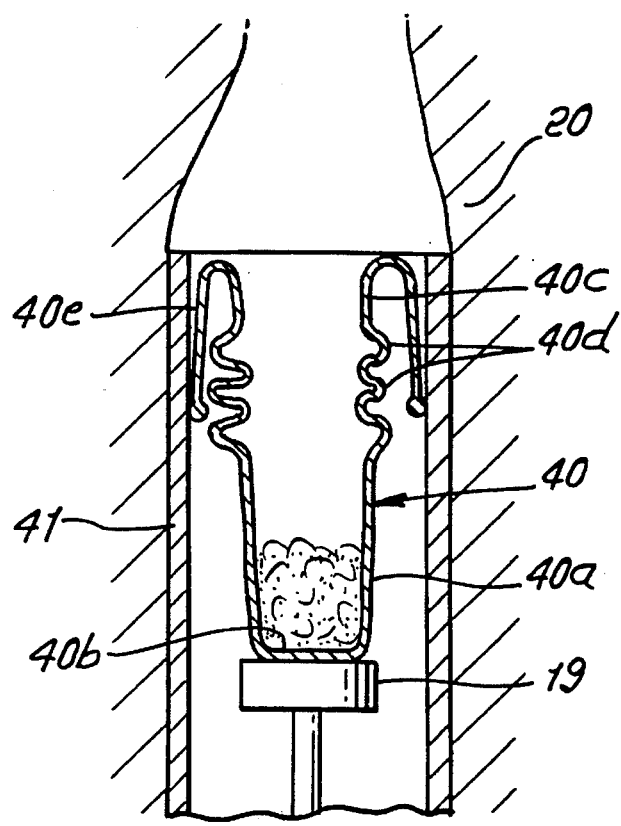
FIG. 9 is a view like FIG. 4 showing a modified device.
Figure 11:
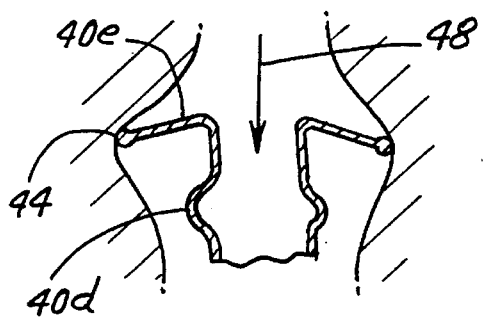
FIG. 11 is a view like FIG. 6 showing the FIG. 9 device self-deployed outwardly, no sleeve arms being used.
Figure 12:
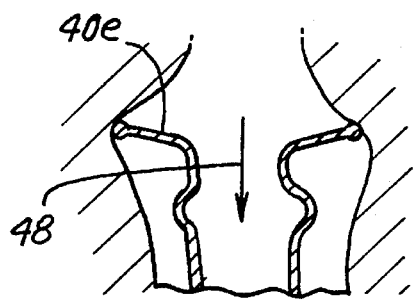
FIG. 12 is a view like FIG. 11 showing a further stage of deployment, the insertion tube having been withdrawn.

FIG. 9 shows the generally tubular, non-flaccid, thin-walled device 40 having lower, tubular side wall 40a and bottom wall 40b forming a receptacle for menstrual flow. The tubular upper side wall extent 40c defines annular corrugations at 40d which seek to restore from vertically collapsed condition within insertion tube 41, to expanded or extended condition, as seen in FIGS. 11 and 12, after tube 41 is withdrawn. Corrugations 40d are "springy" and yieldably resiliently resist compression. The tubular uppermost extent 40e is forcibly and yieldably resiliently turned down in FIG. 9, within tube 41, so that side wall extents 40a and 40c are downwardly re-entrant. Uppermost extent 40e may comprise overlapping leaves, as shown in FIG. 1a in order to maintain tubular configuration when freed and expanded to engage against vaginal walls, as in FIGS. 11 and 12.

Figure 10:
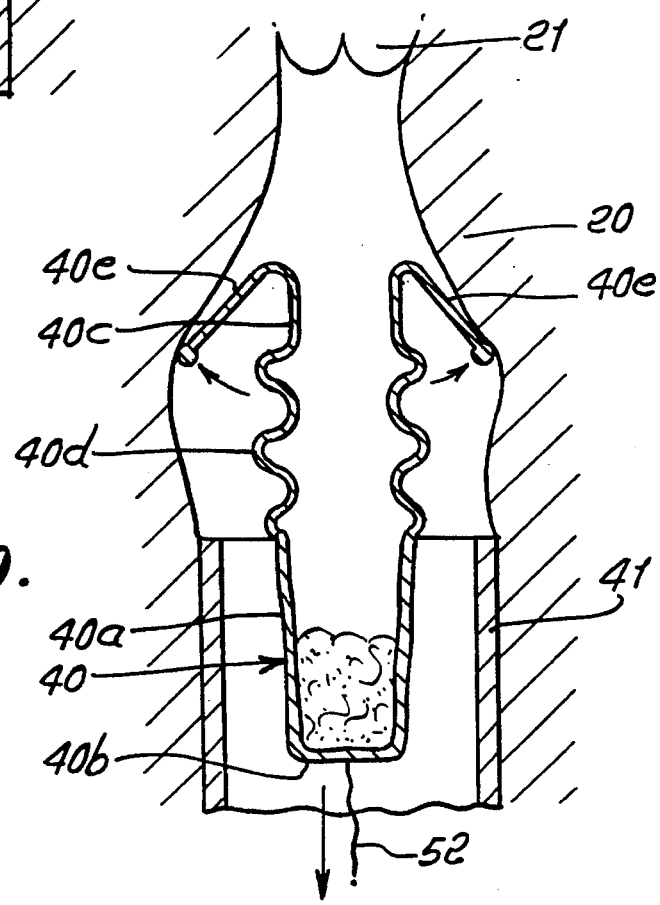
FIG. 10 is a view like FIG. 5 showing the modified device emerging from the insertion tube.

FIG. 10 shows emergence of the device 40 from the insertion tube, as by pusher 19 manipulation to push 40 upwardly, by engagement with wall 40b.

In FIG. 11, the device 40 has completely emerged, and wall extent 40e seeks to deflect outwardly, into sealing engagement with vaginal walls at loci 44. Also, corrugations 40d expand upwardly, to urge device wall or walls 40e upwardly.

In FIG. 12, the tube 41 has been completely withdrawn. Flow into the device is indicated by arrow 48.

Figure 13:
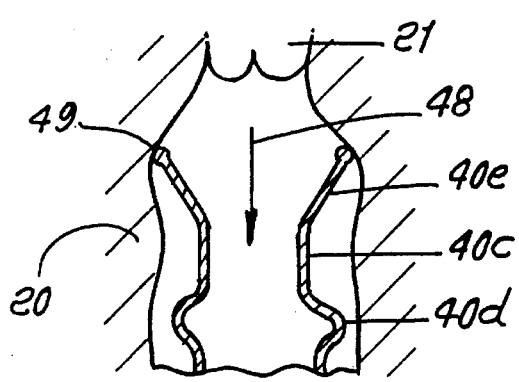
FIG. 13 is a view like FIG. 7, the lower extent of the FIG. 9 device being withdrawn downwardly.

In FIG. 13, partial withdrawal downwardly of the device 40 allows upper extents 40e to maintain sealing engagement, generally annularly, with the vaginal walls at loci 49.

Figure 14:
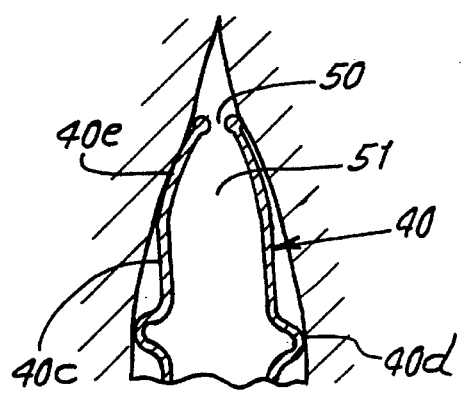
FIG. 14 is a view like FIG. 8 showing the FIG. 9 device with its upper extent self-collapsed to retain collected flow isolated in the device interior.

FIG. 14 shows withdrawal of the entire device 40, the walls 40e self-gathering by material memory restoration action, to press together at 50 and close the device, above its flow-collecting interior 51. A withdrawal string appears at 52.

A representative material of device 40 is silicone or latex.

I claim:

1. A menstrual, flow-controlling tampon comprising, in combination:

a) a generally upright insertion tube having upper and lower ends, b) flow-receiving means positioned within the tube to be bodily displaced and expelled from said upper end of the tube, c) said flow-receiving means, including a thin sheath, and having a deployable portion configured to distend from a downward collapsed position about the sheath to an upwardly deployed condition, to extend into engagement with vaginal walls associated with the cervix, and accommodation to length of vaginal barrel, following its being expelled from the tube, d) and removal means associated with said receiving means to effect withdrawal thereof away from the cervix, whereby upper extent of the deployable portion of the flow-receiving means gathers to retain flow in said flow-receiving means during said withdrawal, e) said flow-receiving means including a flexible film receptacle defining said sheath and opening upwardly toward the cervix and having a flexible wall defining said deployable portion, and a sleeve carrying the receptacle, f) there being structure on the sleeve urging the flexible wall of the receptacle into said deployed condition, said receptacle wall being flaccid, g) and wherein said structure includes multiple memory means self-deployable in bending mode from downward collapsed positions in which said flexible wall of the receptacle fits over the memory means, to self-urged, progressively upwardly deployable position in which said flexible wall is urged against the vaginal walls.

2. The combination of claim 1 wherein said flexible wall defines annular corrugations which are self-expansible, upwardly, in conjunction with said flexible wall being expelled from the tube, allowing self-fitting of the flexible wall to accommodate to the varying lengths of the vaginal barrel.

3. The combination of claim 1 wherein said structure has an upwardly, finally deployed position in which said flexible wall is gathered to isolate flow received in said flow-receiving, flexible film receptacle during said withdrawal.

4. The combination of claim 1 wherein said deployable portion of the flow-receiving means has terminals which self-interengage when gathered to retain flow in the flow-receiving means during said withdrawal.

5. The combination of claim 1 including a plunger within the insertion tube and manipulable to expel the flow-receiving means from the tube.

6. The combination of claim 1 wherein said flexible film is elastomeric.

7. The combination of claim 6 wherein said flexible film consists of latex.

8. A menstrual, flow-controlling tampon comprising, in combination:
   a) a generally upright insertion tube having upper and lower ends,
   b) flow-receiving means positioned within the tube to be bodily displaced and expelled from said upper end of the tube,
   c) said flow-receiving means having a deployable portion configured to distend from a downward collapsed position to an upwardly deployed condition, to extend into engagement with vaginal walls associated with the cervix, and accommodation to length of vaginal barrel, following its being expelled from the tube,
   d) and removal means associated with said receiving means to effect withdrawal thereof away from the cervix, whereby upper extent of the deployable portion of the flow-receiving means gathers to retain flow in said flow-receiving means during said withdrawal,
   e) said flow-receiving means including a flexible film receptacle opening upwardly toward the cervix and having a flexible wall defining said deployable portion, and a sleeve carrying the receptacle,
   f) there being structure on the sleeve urging the flexible wall of the receptacle into said deployed condition, said receptacle wall being flaccid,
   g) and wherein said structure includes multiple memory arms self-deployable in bending mode from downward collapsed positions in which said flexible wall of the receptacle fits over the arms, to self-urged, progressively upwardly deployable positions in which said flexible wall is urged against the vaginal walls.

9. The combination of claim 8 wherein said memory arms have an upwardly, finally-deployed position in which said flexible wall is gathered to isolate flow receive in said flow-receiving, flexible film receptacle during said withdrawal.

10. The combination of claim 9 wherein said arms project in cantilever condition from and above said sleeve in said finally deployed position.

11. The combination of claim 10 wherein said arms have distal end portions that are self-urged toward one another in said finally deployed position.

12. The combination of claim 8 wherein said arms and sleeve have one-piece molded construction.

13. The combination of claim 12 wherein said arms have thickness substantially greater than the thickness of said film.

14. The combination of claim 8 wherein said arms are folded back downwardly alongside said sleeve in said collapsed position.

15. A flow-controlling tampon comprising, in combination:
   a) a generally upright insertion tube having upper and lower ends, and a plunger within said tube, and manipulable proximate the tube lower end,
   b) flow-receiving means positioned within the tube to be bodily displaced and to protrude from said upper end of the tube in response to said manipulation of the plunger,
   c) said flow-receiving means, including a thin sheath, and having a deployable upper portion configured to self distend from a collapsed position to a deployed condition to extend into engagement with vaginal walls associated with the cervix, in response to upward bodily displacement of said flow-receiving means effected by the plunger,
   d) and removal means associated with said receiving means to effect withdrawal thereof away from the cervix, whereby upper extent of the flow-receiving means self collapses to retain flow in said flow-receiving means during said withdrawal;
   e) said flow-receiving means upper portion being in downwardly collapsed condition about the sheath prior to said upward bodily displacement thereof.

16. The combination of claim 15 wherein said flow-receiving means includes flow absorbent material and said thin sheath extends about said flow absorbent material, and said sheath being non-absorbent to said flow, to prevent absorbent material contact with vaginal walls.

17. The combination of claim 16 wherein said sheath consists of molded plastic material, and has an upper open end to receive the flow, and a closed lower end.

18. The combination of claim 16 including a stem attached to said plunger, and extending proximate said lower end of the tube, for pushing said plunger to expel said flow-receiving means from the tube.

19. The combination of claim 15 wherein said sheath has cup configuration.

20. The combination of claim 15 wherein said upper portion of said flow-receiving means is a self-expansible and self-contractible bag.

21. A flow-controlling tampon comprising, in combination:
   a) a generally upright insertion tube having upper and lower ends, and a plunger within said tube, and manipulable proximate the tube lower end,
   b) flow-receiving means positioned within the tube to be bodily displaced and to protrude from said upper end of the tube in response to said manipulation of the plunger,
   c) said flow-receiving means having a deployable upper portion configured to self distend from a collapsed position to a deployed condition to extend into engagement with vaginal walls associated with the cervix, in response to upward bodily displacement of said flow-receiving means effected by the plunger,
   d) and removal means associated with said receiving means to effect withdrawal thereof away from the cervix, whereby upper extent of the flow-receiving means self collapses to retain flow in said flow-receiving means during said withdrawal,
   e) said flow-receiving means including flow absorbent material and a thin sheath about said flow absorbent material and which is non-absorbent to said flow, to prevent absorbent material contact with vaginal walls, f) and including a tubular guide receiving said sheath, said flow-receiving means deployable upper portion having a downwardly collapsed condition in which it extends alongside said tube.

22. The combination of claim 21 wherein said sheath extends in said tubular guide, to slide endwise thereof.

23. The combination of claim 22 wherein said tubular guide slidably retains sheath in the guide.

24. The combination of claim 23 wherein said upper portion of said flow-receiving means forms a flow-receiving pocket immediately above said flow absorbent material.

* * * * *